United States Patent
Stopper et al.

(10) Patent No.: US 9,506,859 B2
(45) Date of Patent: Nov. 29, 2016

(54) METHOD AND DEVICE FOR DETERMINING A VISUAL RANGE IN DAYTIME FOG

(71) Applicant: Robert Bosch GmbH, Stuttgart (DE)

(72) Inventors: Ulrich Stopper, Gerlingen (DE); Stephan Lenor, Stuttgart (DE); Stefan Weber, Saratoga, CA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 14/777,188

(22) PCT Filed: Feb. 24, 2014

(86) PCT No.: PCT/EP2014/053498
§ 371 (c)(1),
(2) Date: Sep. 15, 2015

(87) PCT Pub. No.: WO2014/139783
PCT Pub. Date: Sep. 18, 2014

(65) Prior Publication Data
US 2016/0025627 A1    Jan. 28, 2016

(30) Foreign Application Priority Data
Mar. 15, 2013 (DE) .......... 10 2013 204 597

(51) Int. Cl.
| | |
|---|---|
| *G01N 21/47* | (2006.01) |
| *B60R 16/023* | (2006.01) |
| *G01N 21/53* | (2006.01) |
| *G06K 9/00* | (2006.01) |
| *G01J 1/44* | (2006.01) |
| *G01W 1/00* | (2006.01) |

(Continued)

(52) U.S. Cl.
CPC ........... *G01N 21/47* (2013.01); *B60R 16/0237* (2013.01); *G01J 1/44* (2013.01); *G01N 21/538* (2013.01); *G01W 1/00* (2013.01); *G06K 9/00791* (2013.01); *G01N 2015/0026* (2013.01); *G01N 2015/0693* (2013.01); *G01N 2201/0616* (2013.01); *G01N 2201/126* (2013.01)

(58) Field of Classification Search
None
See application file for complete search history.

(56) References Cited

FOREIGN PATENT DOCUMENTS

DE    60313287    12/2007

OTHER PUBLICATIONS

Dumont, Eric, Nicolas Hautière, and Romain Gallen. "A semi-analytic model of fog effects on vision." Atmospheric Turbulence, Meteorological Modeling and Aerodynamics.—Nova Science, New-York (2010): 635-670.*

(Continued)

*Primary Examiner* — Stephen R Koziol
*Assistant Examiner* — Raphael Schwartz
(74) *Attorney, Agent, or Firm* — Norton Rose Fulbright US LLP; Gerard Messina

(57) ABSTRACT

A method is provided for determining a visual range in daytime fog, the method (800) including a step of reading in and a step of ascertaining. In the step of reading in, coordinates of at least one characteristic point of a brightness curve of a camera image of the fog are read in. The brightness curve represents brightness values of image points of the camera image along a reference axis of the camera image. In the step of ascertaining, a meteorological visual range in the camera image is ascertained using the coordinates, a meteorological contrast threshold, and a processing specification, in order to estimate the visual range in fog. The processing specification images location-dependent and/or direction-dependent scattered light through the fog in the camera image.

12 Claims, 5 Drawing Sheets

(51) Int. Cl.
  *G01N 15/00* (2006.01)
  *G01N 15/06* (2006.01)

(56) References Cited

OTHER PUBLICATIONS

International Search Report for PCT/EP2014/053498, issued on Apr. 22, 2014.
Lenor Stephan et al: "An Improved Mode for Estimation the Meteorological Visibility from a Road Surface Luminance Curve", 2013, The Semantic Web—ISWC 2004; [Lecture Notes in Computer Science]; Springer Erlin Heidelberg; Berlin; Heidelberg; pp. 184-193.
Nicolas Hautiere et al: "Automatic fog detection and estimation of visibility distance through use of an onboard camera", Machine Vision and Applications, Springer, Berlin, DE, Bd. 17, Nr. 1, 2006, pp. 8-20.
Urheim H: "Der photometrische Kontrast als Basisgröβsse für die Sichtmessung /// The photometric contrast as a basic value for visibility measurement", Optik, Wissenschftliche Verlag Gmbh, DE, Bd. 56, Nr. 3, 1980, pp. 253-262.
Tripathi A K et al: "Single image fog removal using anisotropic diffusion", IET Image Processing, IET, UK, Bd. 6, Nr. 7, 2012, pp. 966-975.
Joseph P. Pichamuthu: "Directional variation of visual range due to anisotropic atmospheric brightness", Applied Optics, Bd. 44, Nr. 8, 2005, pp. 1464.

\* cited by examiner

METHOD AND DEVICE FOR DETERMINING A VISUAL RANGE IN DAYTIME FOG

FIELD OF THE INVENTION

The present invention relates to a method for determining a visual range in daytime fog, a corresponding device, and a corresponding computer program product.

BACKGROUND INFORMATION

A reduction of a visual range, for example, due to fog, may be assessed by an observer only via empirical values. To support the observer, a visual range may be determined in an automated manner based on an image of the fog.

German Patent No. 603 13 287 T2 describes a method for visual range determination and fog detection.

SUMMARY

Against this background, the present invention provides a method for determining a visual range in daytime fog, furthermore, a device which uses this method, and finally, a corresponding computer program product.

In fog, water droplets interact with each other. Each water droplet scatters incident light and emits superimposed light in an emission characteristic in the direction of other water droplets. Since the incident light strikes the water droplet from any direction, a brightness of all incident light also influences a brightness of the emitted light. Overall, an emitted light quantity is similar in magnitude to an incident light quantity. A dark area reflects little incident ambient light. A water droplet which is situated near the dark area is illuminated with little light from the direction of the dark area. However, from an opposite direction, the water droplet is illuminated with the ambient light. The water droplet emits light with a lower intensity than another water droplet which is illuminated with the ambient light from all directions. The farther a water droplet is from the dark area, the greater the number of other water droplets which are situated between the dark area and the water droplet. Thus, the influence of the light emitted by the other water droplets on the overall light striking the water droplet increases with increasing distance from the dark area. Therefore, for determining a visual range near the ground, for example, from the point of view of a vehicle or from the point of view of a monitoring camera, it is advantageous to describe the fog using location-dependent and/or direction-dependent characteristics, in order to be able to draw conclusions about the visual range using a model of the fog.

A method is introduced for determining a visual range in daytime fog, the method including the following steps:

reading in coordinates of at least one characteristic point of a brightness curve of a camera image of the fog, the brightness curve representing brightness values of image points of the camera image along a reference axis of the camera image; and ascertaining a meteorological visual range in the camera image using the coordinates, a meteorological contrast threshold, and a processing specification, in order to estimate the visual range in fog, the processing specification imaging location-dependent and/or direction-dependent scattered light through the fog in the camera image.

Furthermore, a device is introduced for determining a visual range in daytime fog, the device having the following features:

a device for reading in, which is designed to read in coordinates of at least one characteristic point of a brightness curve of a camera image of the fog, the brightness curve representing brightness values of image points of the camera image along a reference axis of the camera image; and a device for ascertaining, which is designed to ascertain a meteorological visual range in the camera image using the coordinates, a meteorological contrast threshold, and a processing specification, in order to estimate the visual range in fog, the processing specification being designed to image location-dependent and/or direction-dependent scattered light through the fog in the camera image.

A visual range may be understood to mean a distance across which an object is barely visible. The meteorological visual range is the distance across which an object having a high contrast is barely visible. The meteorological visual range may be defined as the minimum contrast via a meteorological contrast threshold. The contrast may be between a color of the object and a background or surroundings of the object, and alternatively or in addition, may be the contrast between at least two adjacent colors of the object. For example, the object may have two adjacent color areas which are colored in contrasting colors, for example, black and white. Likewise, the object may be at least partially colored in a color which contrasts with the surroundings of the object. The visual range of an object having low contrast may be lower than the meteorological visual range. For example, fog may be made up of fine water droplets, and alternatively or in addition, particles, distributed in the air. The water droplets/particles may scatter and absorb light striking them. The light may be daylight and, alternatively or in addition, light from the object. The water droplets/particles have an emission characteristic which is a function of an incidence direction of the particular light beam. Emission characteristics of a plurality of light beams from different incidence directions are superimposed at an individual water droplet/particle. The resulting emission characteristics of all water droplets/particles along an optical path between an observer and the object are superimposed on each other. The greater the number of water droplets/particles which are situated in the optical path, the more the contrast of the object is reduced for the observer. If the contrast is reduced below a threshold value, the observer is no longer able to perceive the object. It follows that the denser the fog is, the lower the visual range is. A camera image may be configured from image points in a grid made up of rows and columns. The camera image may be taken by a camera in whose detection area the fog is situated. A brightness value may be assigned to each image point. A brightness curve may be plotted in a diagram. A location of the image points in the camera image may be plotted on a first coordinate axis of the diagram. A brightness value of the image points of the camera image may be plotted on a second coordinate axis. Coordinates of a characteristic point may be coordinate values of a point on the brightness curve which describe the curve in a comprehensible manner. For example, the characteristic point may be an inflection point of the brightness curve at which a curvature behavior of the brightness curve changes. A reference axis may be a virtual line in the camera image, along which the image points plotted in the diagram are situated in the camera image. In particular, the reference axis may be situated centrally in the camera image. A processing specification may image a theoretical fog model of ideal fog as a function of at least the coordinates of the characteristic point. The meteorological visual range may be ascertained via the processing specification and the contrast threshold, even if no object having high contrast is imaged in the camera.

A device may presently be understood to be an electrical device which processes sensor signals and outputs control and/or data signals as a function of them. The device may have an interface which may have a hardware-based and/or software-based design. In a hardware-based design, the interfaces may, for example, be part of a so-called system ASIC which includes a wide variety of functions of the device. However, it is also possible that the interfaces are self-contained integrated circuits or are made up at least partially of discrete elements. In a software-based design, the interfaces may be software modules which, for example, are present on a microcontroller, in addition to other software modules.

In the step of reading in, coordinates of at least one additional characteristic point of the brightness curve may be read in. The meteorological visual range may furthermore be ascertained using the coordinates of the additional characteristic point. The brightness curve may be described with a greater certainty via a second point.

In the step of reading in, a plurality of coordinates of characteristic points of the brightness curve may be read in. With more points of the brightness curve, even an irregular profile of the brightness curve may be imaged.

The scattered light may be modeled via a superimposition of a location-dependent, and alternatively or in addition, direction-dependent interspersed ambient light in an optical path between an object and an observer. The object may, for example, be a background such as a road or an object on the road. The ambient light may be daylight which is interspersed diffusely. The interspersed ambient light may increase with increasing distance from the ground. The image may be light reflected on the object. By modeling the location-dependent and, alternatively or in addition, direction-dependent interspersing, it may be taken into account that the farther away the ground is, the brighter the fog is.

The processing specification may image a relationship between the coordinates and an extinction coefficient of the fog in the camera image, the extinction coefficient in particular representing a distance-related decrease in an optical contrast in the fog. The extinction coefficient may describe a density of the fog. The extinction coefficient may be independent of the ambient light. The extinction coefficient may be directly related to the meteorological visual range via the meteorological threshold value. The fog may be simply and accurately characterized via the extinction coefficient.

A result of the processing specification may be read out of a table, for example, a lookup table. A lookup table may be a predetermined and stored lookup table. A plurality of parameter-dependent results may be stored in the lookup table. The lookup table may be multidimensional. A lookup table allows the result to be read out very rapidly without carrying out time-intensive computing operations which may also be repetitive. The results in the lookup table may be interpolated. An interpolation allows a quantity of data in the lookup table to be reduced and the result to be output more rapidly. Different trial functions may be selected for the interpolation. For example, polynomials may be used. Depending on the requirement for the fog detection, different polynomials may determine an approximation quality of the fog model. Depending on the requirement, an adapted polynomial may be used.

The meteorological visual range may furthermore be ascertained using at least one parameter of a camera generating the camera image. For example, at least one optical parameter, such as a focal distance, a number of rows and/or columns, an image error, or a decrease in sensitivity may be taken into account. Likewise, at least one mechanical parameter, such as an initial height above the ground, an initial viewing angle of the camera, a change in height from the initial height, a change in viewing angle from the initial viewing angle, or a horizon position may be taken into account. The processing specification may be evaluated more robustly and provide more reliable results using at least one parameter.

In the step of reading in, furthermore, the at least one parameter may be variable and read in from the camera. Using at least one variable parameter, changes from camera image to camera image may be detected and the meteorological visual range may be ascertained reliably, despite changes in the detection area of the camera.

The meteorological visual range may furthermore be ascertained using at least one additional parameter of fog droplets of the fog. The additional parameter may be variable. In particular, the additional parameter may be variable within a value range. To simplify the processing specification, the additional parameter may be set to a fixed value within the value range. The composition of the fog and, alternatively or in addition, the emission characteristic of the water droplets/particles of the fog, may be modeled more accurately using the additional parameter. In particular, the additional parameter may be a backscatter parameter which describes the location-dependent and/or direction-dependent interspersion of light via the water droplets/particles.

The coordinates may be read in from a brightness curve along a vertical reference axis. The reference axis may in particular be detected in the center of the camera image, parallel to a side edge of the camera image. A particularly meaningful brightness curve may be detected on the vertical reference axis. Multiple brightness curves may also be detected on different reference axes. Thus, a redundancy may be generated if no meaningful brightness curve is able to be detected on one of the reference axes in the camera image. The reference axis may also be a reference range. The reference axis may contact at least one point per image row. One value for the brightness is plotted on the brightness curve for each of the points. In the case of more than one image point per row, a median or mean of all image points taken into account in the image row may be formed in order to obtain a shared brightness value. The points which image the road and the sky may be pre-segmented.

A computer program product including program code which may be stored on a machine-readable carrier such as a semiconductor memory, a hard-disk memory, or an optical memory, and which is used for carrying out the method according to one of the specific embodiments described above, is also advantageous if the program product is executed on a computer or a device.

DETAILED DESCRIPTION

Figure 1:
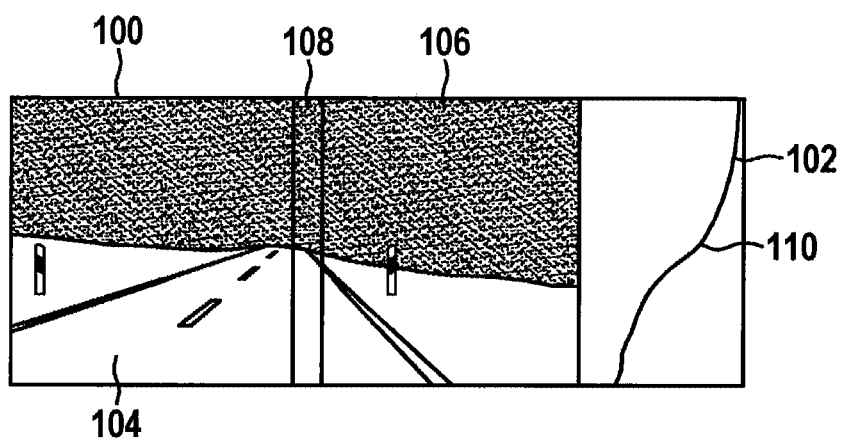
FIG. 1 shows a representation of a camera image including a brightness curve.

In the following description of advantageous exemplary embodiments of the present invention, identical or similar reference numerals are used for the elements depicted in the various figures and acting similarly, a repeated description of these elements being omitted.

FIG. 1 shows a representation of a camera image 100 including a brightness curve 102. The camera image 100 is taken from a perspective of a driver of a road vehicle and shows a road 104 which is shrouded by fog 106 in an image center. The visual conditions are significantly limited. Fog 106 is homogeneous. Brightness curve 102 is situated next to camera image 100. Brightness curve 102 or luminance curve is plotted in a diagram on whose abscissa a normalized brightness value between zero and 100 percent is plotted and on whose ordinate image rows of camera image 100 are plotted. An origin of the coordinate system matches a right lower corner of camera image 100. The ordinate is scaled in such a way that the image rows of camera image 100 match the corresponding image rows of the coordinate system. Brightness curve 102 relates to a vertical image strip 108 which is oriented centrally in camera image 100 and extends from a lower image edge to an upper image edge. Image strip 108 images road 104 up to the horizon and then the sky. In image strip 108, road 104 is imaged at high contrast at the lower image edge. A brightness of road 104 increases through fog 106 with increasing height in the image strip 108, until road 104 is no longer distinguishable from fog 106 approximately in the image center. As a result, in image 100, the sky extends deep into image 100. The brightness values in image 100 are generated via a linear imaging specification from the real brightness values or the physical luminance of the objects or illuminance on the sensor surface. This may be identified in brightness curve 102 by an increase of the brightness from image row to image row. From the image center upwards, only fog 106 is imaged in image strip 108. The brightness in image strip 108 continues to increase with increasing height above road 104 up to the upper image edge. Brightness curve 102 has an S-shaped profile corresponding to the image brightness in image strip 108. The brightness curve has an inflection point $v_i$ 110. Coordinates of inflection point $v_i$ 110 may easily be estimated from brightness curve 102.

The model introduced here improves an existing model and a resulting algorithm for visual range estimation with the aid of a monocular camera having a view toward a flat roadway 104 up to the horizon.

In the case of a monocular and intensity-based camera on an almost flat and sufficiently free roadway 104, Hautière et al. derived a model-based algorithm for estimating the meteorological visual range. A camera oriented toward road 104 up to the horizon images (using a linear camera model) brightness profile 102 of road 104 up to the horizon, as in FIG. 1. It is found that this brightness curve 102 always has an inflection point $v_i$ and that there is a parameter-dependent relationship of $v_i$ to the meteorological visual range. This algorithm is essentially based on Koschmieder's model of the exponential mixing of light on the optical path from the object to the observer, $$L = e^{-Kd}L_0 + (1-e^{-Kd})L_{air}$$

where parameter $L_0$ represents the luminance of the object and parameter $L_{air}$ represents the ambient light and d [m] represents the distance between the object and the observer. As the extinction coefficient, K [1/m] is the critical fog parameter, which represents the meteorological visual range $d_{met}$ [m].

$$d_{met} = -\frac{\log_e(0.05)}{K}$$

However, if the class of Koschmieder's model curves is observed, $$v \mapsto L_{L_0,L_{air}}K(v)$$

they are not sufficient for describing measured luminance curves 102, since Koschmieder's model assumes a constant, direction-independent ambient light. Therefore, a significant error in the visual range estimation may be expected based on this model.

The approach introduced here describes an improved model of the situation which takes into account the effects of nonconstantly and anisotropically interspersed light. In addition, it is shown that this more complex model is also suitable for use in real-time systems and for use in an algorithm of the same type as Hautière.

A relative improvement of the visual range estimation of approximately 5% to 30% is achieved, depending on the distance. Thus, a significant systematic error is corrected.

Figure 2:
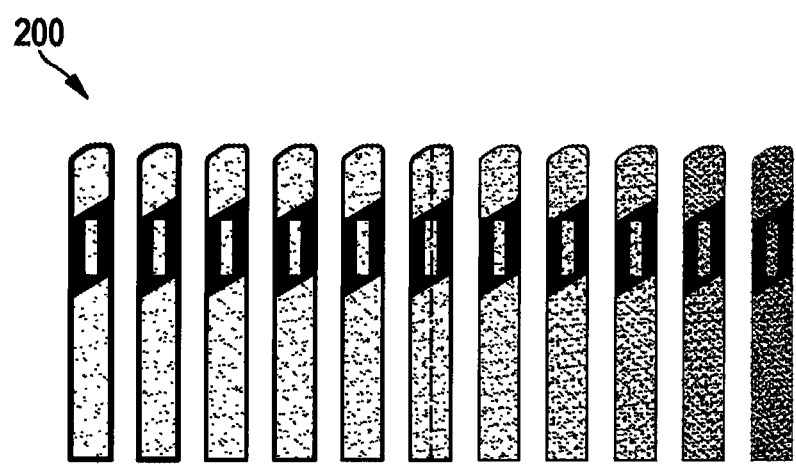
FIG. 2 shows a representation of reflector posts having decreasing contrast due to different distances in fog.

FIG. 2 shows a representation of reflector posts 200 having a decreasing contrast due to different distances in fog. The reflector posts are shown at a distance of 10 meters from each other and in a range of between zero meters and 100 m away from an observer. Here, the meteorological visual range is 50 m. Here, the meteorological visual range is defined by the undershooting of a contrast threshold by 5% for a black object against the horizon. Thus, 50 meters correspond to an extinction coefficient of the fog of approximately 0.06 m$^{-1}$. Reflector post 200 at zero meters has a contrast of 100% of the original contrast of the reflector post against the horizon. The post is white and the band is black. At 10 meters, reflector post 200 has a contrast of 55% of the original contrast. The post is light gray and the band is dark gray. At 20 meters, reflector post 200 has a contrast of 30% of the original contrast. At 30 meters, reflector post 200 has a contrast of 17% of the original contrast. At 40 meters, reflector post 200 has a contrast of 9.1% of the original contrast. At 50 meters, reflector post 200 has a contrast of 5% of the original contrast. Here, the meteorological contrast threshold has been reached. Because of its maximally high-contrast characteristic, the contrast between the white and the black of the reflector post is always somewhat greater than the contrast of a black object with the background, via which the visual range threshold is defined. At 50 meters, the post has a contrast of 5.52%, which is somewhat higher than the 5% contrast of a black object with the background. At a 5% contrast of a black object with the background/horizon, the meteorological visual range is defined. At 60 meters, reflector post 200 has a contrast of 2.7% of the original contrast. At a distance of 60 meters from the observer, the reflector post 200 may be perceived only with great effort. At a greater distance, it is no longer possible to detect the reflector post. At 70 meters, reflector post 200 has a contrast of 1.5% of the original contrast. At 80 meters, reflector post 200 has a contrast of 0.83% of the original contrast. At 90 meters, reflector post 200 has a contrast of 0.46% of the original contrast. At 100 meters, reflector post 200 has a contrast of 0.25% of the original contrast.

The visible light of an object is highly modified by transmission through fog. At every fog droplet, the light is scattered on the one hand and is enhanced by interspersed extraneous light on the other hand. The consequence is an exponential weakening of the contrast with increasing distance, resulting in a distance-dependent limitation for visual systems. Legislative bodies therefore prescribe driving with low-beam headlights in daytime fog and allow switching on fog lights. Rear fog lights are allowed to be switched on at visual ranges below 50 m (German Traffic Regulation, Section 17, Subsection 3). In addition, drivers must adjust their speed to the visual range (German Traffic Regulation, Section 3, Subsection 1). In order to be able to carry out the lighting control and adaptive speed control autonomously and/or support the driver in the difficult estimation of the visual range, it is practical for the visual range to be estimated by vehicle sensors.

Figure 3:
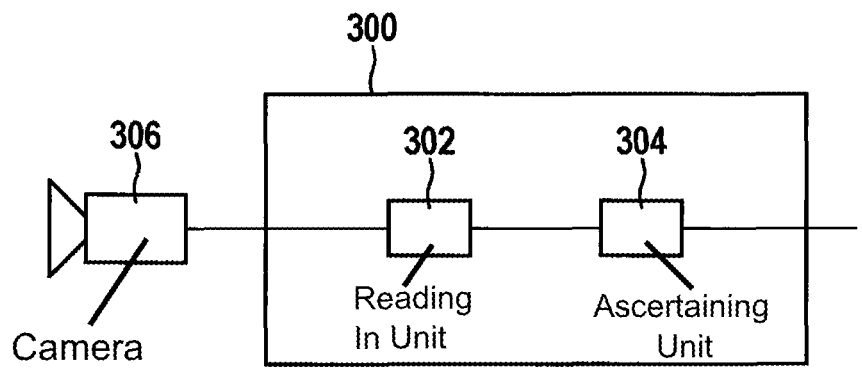
FIG. 3 shows a block diagram of a device for determining a visual range in daytime fog according to one exemplary embodiment of the present invention.

FIG. 3 shows a block diagram of a device 300 for determining a visual range in daytime fog according to one exemplary embodiment of the present invention. Device 300 has a unit 302 for reading in and a unit 304 for ascertaining Device 300 is connected to a camera 306. Camera 306 provides an inflection point coordinate of an inflection point as a characteristic point of a brightness curve of a camera image of camera 306, which is oriented toward the fog. The brightness curve represents brightness values of image points of the camera image along a reference axis of the camera image. Unit 302 for reading in is designed to read in the inflection point coordinate. Unit 304 for ascertaining is designed to ascertain a meteorological visual range in the camera image using the inflection point coordinate, a meteorological contrast threshold, and a processing specification, in order to estimate the visual range in fog. The processing specification images location-dependent and/or direction-dependent scattered light through the fog in the camera image.

In one exemplary embodiment, the scattered light is modeled by superimposing location-dependent and/or direction-dependent interspersed ambient light into an optical path between an object and an observer. As a result, the influence of a height above a dark area on the fog may be taken into account.

In one exemplary embodiment, in the processing specification, a relationship between the inflection point coordinate and an extinction coefficient of the fog is imaged in the camera image. The extinction coefficient represents a distance-dependent decrease in an optical contrast in the fog.

In one exemplary embodiment, in unit 304 for ascertaining, a result of the processing specification is read out of a lookup table. The visual range may be ascertained rapidly and efficiently via a lookup table.

In one exemplary embodiment, the meteorological visual range is furthermore ascertained using at least one parameter of the camera. For example, a height of camera 306 above the dark area has a decisive influence on the visual range, since more scattered light is present with increasing distance from the dark area.

In one exemplary embodiment, the parameter is variable and is read in from camera 306. For example, the camera may include an inclination angle sensor or may ascertain its full relative positioning with respect to the road level via a homographic estimation. Likewise, the inflection point coordinate may be output relative to a virtual horizon in the camera image.

In one exemplary embodiment, the meteorological visual range is furthermore ascertained from fog droplets of the fog using at least one additional parameter. The additional parameter may be a function of the particle and droplet distribution in the fog. The additional parameter may be set to a fixed value with low loss of accuracy of the processing specification.

In one exemplary embodiment, the inflection point coordinate is read in from a brightness curve along a vertical reference axis. The brightness curve is particularly pronounced in particular on the vertical axis. As a result, the inflection point coordinate may be detected in a particularly simple manner with the vertical reference axis.

Figure 4:
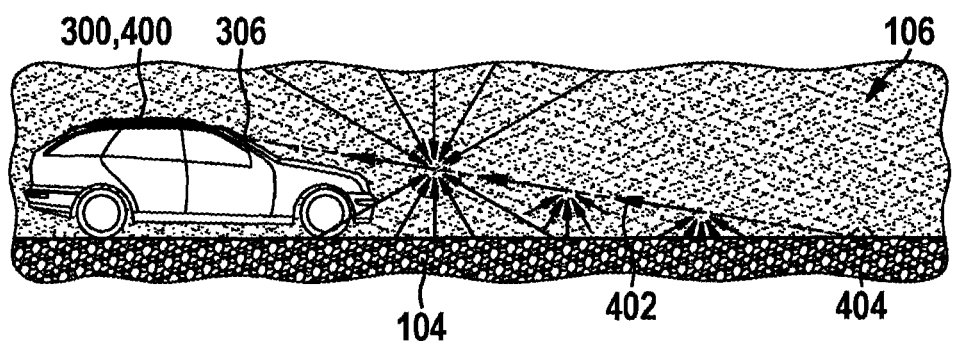
FIG. 4 shows a representation of a vehicle including a device according to one exemplary embodiment of the present invention.

FIG. 4 shows a representation of a vehicle 400 including a device 300 according to one exemplary embodiment of the present invention. Vehicle 400 is present in homogeneous fog 106 on a road 104. Road 104 and fog 106 are detected in a camera image, for example, as shown in FIG. 1 by a camera 306 oriented forward. For example, in FIG. 4, an optical path 402 is plotted. Optical path 402 runs from a point 404 on the surface of road 104 to camera 306 through fog 106. Optical path 402 is at an acute angle to road 104. Optical path 402 moves continuously away from the surface of road 104 from point 404 to camera 306. The farther optical path 402 is from the surface, the greater the volume of fog 106 which surrounds optical path 402, on the surface side as well. Near road 104, the fog droplets are almost exclusively illuminated from above, since the surface is dark, i.e., almost completely absorbs ambient light. As a result, the fog droplets near road 104 itself emit relatively little light. The farther the fog droplets are from road 104, the more they are also illuminated by fog droplets situated between them and the road and the more they emit light themselves. The emission of light by all fog droplets on optical path 402 amounts to the total location-dependent and/or direction-dependent scattered light which causes point 404 to seem significantly brighter than it actually is.

The improved model introduced here integrates the light changes over total optical path 402 into the route parameter s and models the interspersed light $L_{in}$ in a direction-dependent manner, for example, with the aid of Koschmieder and the assumption of a simplified scene as shown in FIG. 4. The interspersed light is generally not constant over the optical path. The direction-dependent portion of the interspersed light, which is further scattered into the optical path, is modeled via an anisotropic phase function $\psi$ like the one of Henyey and Greenstein. A resulting equation may be processed using numerics.

$$L(\sigma,d) = e^{Kd}L_0 + \int_0^d Ke^{-Ks}\int_{g^2} L_{in}(\omega,s)\psi(\sigma,\omega)dS(\omega)ds$$

The phase function may also be replaced by other phase functions which sufficiently describe the scattering behavior in fog. Parameters of such phase functions may be rediscussed within the scope of an algorithm, analogously to the additional parameters describing the fog.

Figure 5:
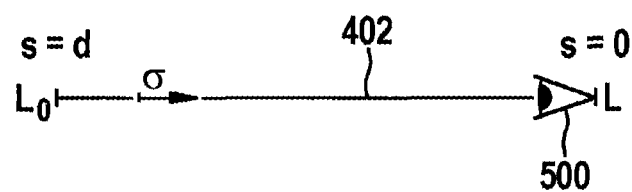
FIG. 5 shows a representation of an optical path according to one exemplary embodiment of the present invention.

FIG. 5 shows a representation of an optical path 402 according to one exemplary embodiment of the present invention. Here, optical path 402 is schematically depicted and extends as in FIG. 4 between an object and an observer 500. The object has an initial luminance $L_0$ and is situated at a distance d from observer 500. Route parameter s falls linearly along the optical path from d at the object to 0 at the observer. Optical path 402 has a space vector σ which is oriented toward observer 500 here. Along optical path 402, the luminance of the object is weakened by the fog and enhanced by interspersed light. It reaches observer 500 having a luminance L.

Figure 6:
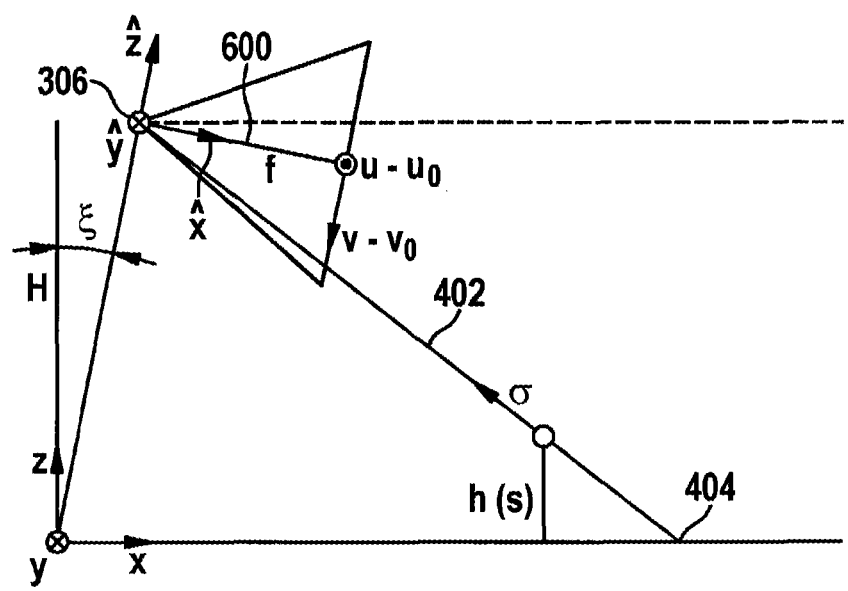
FIG. 6 shows a representation of geometric camera parameters according to one exemplary embodiment of the present invention.

FIG. 6 shows a representation of geometric camera parameters according to one exemplary embodiment of the present invention. Here, camera 306 is only depicted symbolically. Camera 306 is situated at a height H above the ground. A sensor level and thus an optical axis 600 of camera 306 are tipped at an angle ζ with respect to a reference coordinate system x y z. As a result, camera 306 has a camera coordinate system $\hat{x}$ $\hat{y}$ $\hat{z}$. Optical axis 600 matches $\hat{x}$. Image coordinates of a camera image of camera 306 are designated two-dimensionally by u and v based on a center point $u_0$, $v_0$ on optical axis 600, where u characterizes the lateral direction and v characterizes the vertical direction. Center point $u_0$, $v_0$ is situated at a distance f from camera 306, f being a focal distance of the camera. Camera 306 corresponds to the observer in FIG. 5. Optical path 402 extends between camera 306 and point 404 on the ground. As in FIG. 5, space vector σ is assigned to the optical path. Optical path 402 has a height h(s) above the ground which is a function of route s.

Figure 7:
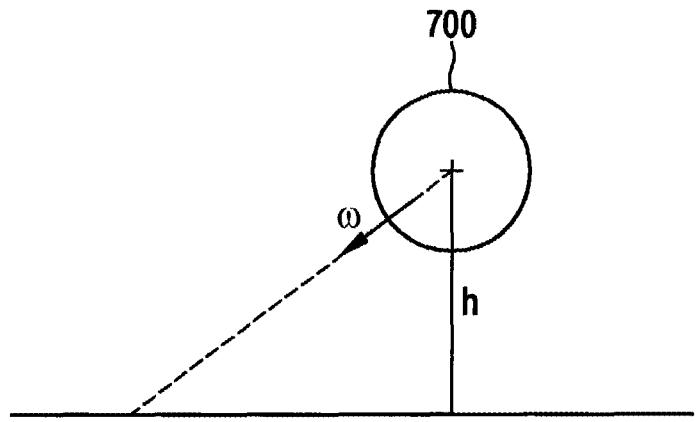
FIG. 7 shows a representation of an interspersion of a light beam from one direction at a water droplet according to one exemplary embodiment of the present invention.

FIG. 7 shows a representation of an interspersion of light at a water droplet 700 according to one exemplary embodiment of the present invention. Water droplet 700 is situated at a height h above the ground. The light interspersed into water droplet 700 is a function of a direction vector ω, which is normalized and points from the droplet center point in the direction of the incident light. The less perpendicular ω is to the surface, the greater the distance is from a surface in direction ω. Thus, the influence of the ambient light also increases as a function of w. In addition, the greater height h is, the greater the influence of ambient light is also on the lower side of the water droplet.

Figure 8:
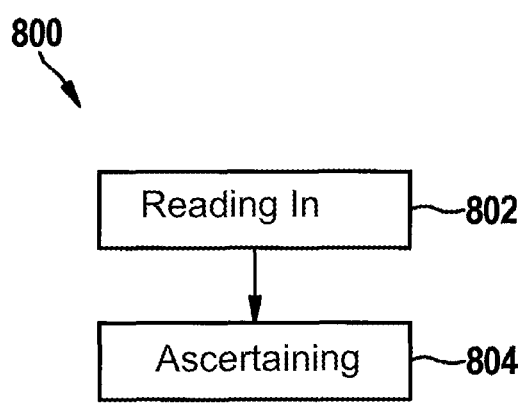
FIG. 8 shows a flow chart of a method for determining a visual range in daytime fog according to one exemplary embodiment of the present invention.

FIG. 8 shows a flow chart of a method 800 for determining a visual range in daytime fog according to one exemplary embodiment of the present invention. Method 800 has a step 802 of reading in and a step 804 of ascertaining. In step 802 of reading in, an inflection point coordinate of an inflection point is read in as the characteristic point of a brightness curve of a camera image of the fog. The brightness curve represents brightness values of image points of the camera image along a reference axis of the camera image. In step 804 of ascertaining, a meteorological visual range in the camera image is ascertained using the inflection point coordinate, a meteorological contrast threshold, and a processing specification, in order to estimate the visual range in fog. The processing specification images location-dependent and/or direction-dependent scattered light through the fog in the camera image.

The approach introduced here may also be used to determine the visual range in a visual field of a static camera, for example, a monitoring camera. Some highly suitable application options of the visual range estimation include, for example, monitoring cameras at airports and monitoring cameras for roads.

Figure 9:
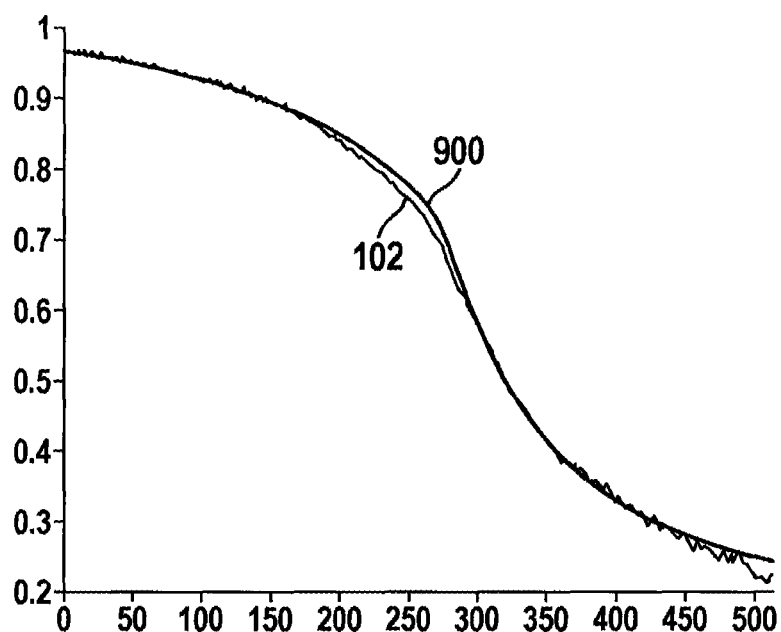
FIG. 9 shows a diagram of an ascertained brightness curve and an adapted model curve according to one exemplary embodiment of the present invention.

FIG. 9 shows a diagram of an ascertained brightness curve 900 according to one exemplary embodiment of the present invention. Ascertained curve 900 is superimposed with a brightness curve 102 as in FIG. 1. Ascertained curve 900 and brightness curve 102 are plotted in a diagram as in FIG. 1. Only reference axes of the diagram are interchanged here. Ascertained curve 900 has been ascertained using a processing specification according to the approach introduced here. Model curve 900 was completely fitted over brightness curve 102. Ascertained curve 900 has a great similarity to brightness curve 102. Ascertained curve 900 has been ascertained using a least-squares error approach. Ascertained curve 900 has been calculated iteratively. As a result, it is possible to reversely infer an extinction parameter of the fog which is based on brightness curve 102. As the determining parameter of the fog, the extinction parameter is responsible for the visual range in the fog.

Figure 10:
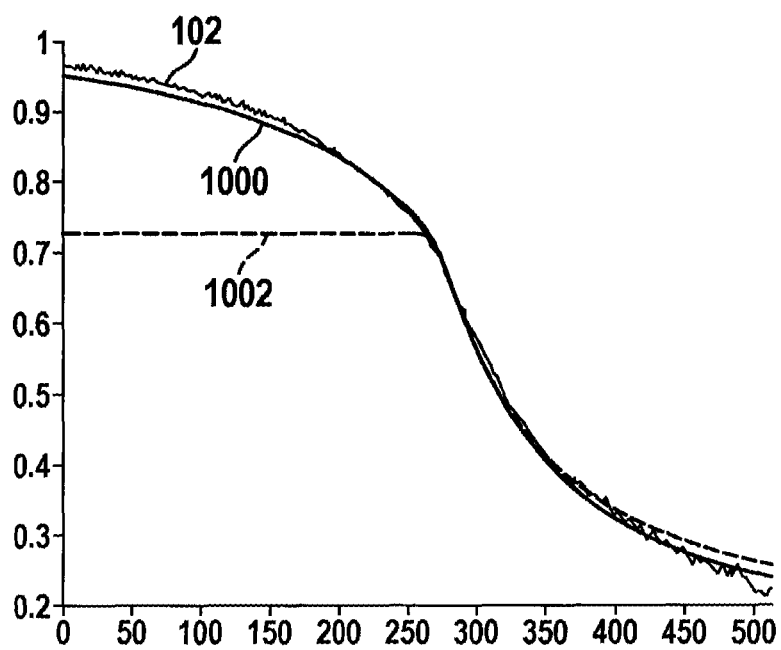
FIG. 10 shows a comparison of an ascertained brightness curve and a model curve adapted in another way according to one exemplary embodiment of the present invention having a different brightness curve.

FIG. 10 shows a comparison of an ascertained brightness curve 1000 according to one exemplary embodiment of the present invention with another brightness curve 1002. As in FIG. 9, ascertained brightness curve 1000 is superimposed with brightness curve 102. Ascertained curve 1000 has been ascertained using a processing specification according to the approach introduced here. Ascertained curve 1000 has a great similarity to brightness curve 102. Ascertained curve 1000 has been ascertained using a lookup table. The lookup table has been ascertained via precalculated curve profiles. One of the curve profiles has been read out of the lookup table corresponding to at least the inflection point coordinates, and the visual range has been ascertained using the extinction parameter of curve 1000 and the meteorological threshold value. The other curve 1002 has been calculated using direction-independent and/or location-independent scattered light.

In the lookup table, simplifications in the case of minimal errors with respect to the iterative calculation may result in a significant reduction in the processing time. For example, parameters having discrete values may be stored in the lookup table. The access to the lookup table and the memory requirement may once again be significantly improved through interpolation using suitable trial functions.

In order to obtain K from $v_i$, the model may be used to calculate which K results in which $v_i$. In addition to $v_i$, K may also be a function of geometric and intrinsic camera parameters. This relationship (for fixed geometric/internal parameters) is bijective. In particular, it is thus also possible to infer K again from the $v_i$. For this complex model, the associated $v_i$ are calculated for all possible K. The calculation is independent of $L_{air}$ and $L_0$. A real luminance curve may then be recorded from the road, the $v_i$ of this curve may be read, and the suitable K which generated this $v_i$ may again be reversely inferred.

The exemplary embodiments described and shown in the figures are selected only by way of example. Different exemplary embodiments may be combined completely or with respect to individual features. One exemplary embodiment may also be supplemented by features of an additional exemplary embodiment.

Method steps according to the present invention may furthermore be repeated and executed in a sequence other than the one described.

If an exemplary embodiment includes an "and/or" link between a first feature and a second feature, this is to be read as meaning that the exemplary embodiment according to one specific embodiment has both the first feature and the second feature and has either only the first feature or only the second feature according to an additional specific embodiment.

What is claimed is:

1. A method for determining a visual range in daytime fog, comprising:

reading in coordinates of at least one characteristic point of a brightness curve of a camera image of the fog, the brightness curve representing brightness values of image points of the camera image along a reference axis of the camera image;

and ascertaining a meteorological visual range in the camera image using the coordinates, a meteorological contrast threshold, and a processing specification, in order to estimate the visual range in fog, the processing specification being designed to model the brightness curve in accordance with at least one of location-dependent scattered light and direction-dependent scattered light through the fog in the camera image.

2. The method as recited in claim 1, wherein in the step of reading in, coordinates of at least one additional characteristic point of the brightness curve are read in, and wherein the meteorological visual range furthermore being ascertained in the step of ascertaining using the coordinates of the additional characteristic point.

3. The method as recited in claim 1, wherein in the step of ascertaining, the scattered light is modeled by superimposing at least one of location-dependent ambient light and direction-dependent interspersed ambient light into an optical path between an object and an observer.

4. The method as recited in claim 1, wherein in the step of ascertaining, the processing specification images a relationship between the coordinates and an extinction coefficient of the fog in the camera image.

5. The method as recited in claim 4, wherein the extinction coefficient represents a distance-dependent decrease in an optical contrast in the fog.

6. The method as recited in claim 1, wherein in the step of ascertaining, a result of the processing specification is read out of a table.

7. The method as recited in claim 1, wherein in the step of ascertaining, the meteorological visual range is furthermore ascertained using at least one parameter of a camera generating the camera image.

8. The method as recited in claim 6, wherein in the step of reading in, furthermore, the at least one parameter is variable and is read in from the camera.

9. The method as recited in claim 1, wherein in the step of ascertaining, the meteorological visual range is furthermore ascertained using at least one additional parameter of fog droplets of the fog.

10. The method as recited in claim 1, wherein in the step of reading in, the coordinates are read in from a brightness curve along a vertical reference axis.

11. A device for determining a visual range in daytime fog, comprising:

a unit for reading in coordinates of at least one characteristic point of a brightness curve of a camera image of the fog, the brightness curve representing brightness values of image points of the camera image along a reference axis of the camera image;

and a unit for ascertaining a meteorological visual range in the camera image using the coordinates, a meteorological contrast threshold, and a processing specification, in order to estimate the visual range in fog, the processing specification being designed to model the brightness curve in accordance with at least one of location-dependent scattered light and direction-dependent scattered light through the fog in the camera image.

12. A non-transitory medium embodying a computer program product including program code for carrying out, if the program product is executed on a device, a method for determining a visual range in daytime fog, comprising:

reading in coordinates of at least one characteristic point of a brightness curve of a camera image of the fog, the brightness curve representing brightness values of image points of the camera image along a reference axis of the camera image;

and ascertaining a meteorological visual range in the camera image using the coordinates, a meteorological contrast threshold, and a processing specification, in order to estimate the visual range in fog, the processing specification being designed to model the brightness curve in accordance with at least one of location-dependent scattered light and direction-dependent scattered light through the fog in the camera image.

* * * * *